(12) United States Patent
Gruebele et al.

(10) Patent No.: US 8,757,871 B2
(45) Date of Patent: Jun. 24, 2014

(54) PARTICLE DYNAMICS MICROSCOPY USING TEMPERATURE JUMP AND PROBE ANTICORRELATION/CORRELATION TECHNIQUES

(75) Inventors: Martin Gruebele, Champaign, IL (US); Simon Ebbinghaus, Hagen (DE); Apratim Dhar, Urbana, IL (US); J Douglas McDonald, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 349 days.

(21) Appl. No.: 13/210,942

(22) Filed: Aug. 16, 2011

(65) Prior Publication Data

US 2012/0039353 A1 Feb. 16, 2012

Related U.S. Application Data

(60) Provisional application No. 61/374,001, filed on Aug. 16, 2010.

(51) Int. Cl.
*G01B 9/04* (2006.01)
*G01N 25/00* (2006.01)
*G01N 25/20* (2006.01)

(52) U.S. Cl.
USPC ............. 374/45; 374/101; 374/132; 374/141; 382/312; 250/336.1; 356/335; 356/904

(58) Field of Classification Search
USPC ............. 374/29, 30, 137, 102, 101, 104, 109, 374/111, 112, 115, 45, 163, 166, 167, 4, 5, 374/32, 10, 141, 121, 122; 382/312; 356/335, 904; 250/336.1
See application file for complete search history.

(56) References Cited

U.S. PATENT DOCUMENTS 4,168,881 A * 9/1979 Rosenberger ................. 359/381
4,700,298 A * 10/1987 Palcic et al. .................. 382/128

(Continued)

OTHER PUBLICATIONS

Gruebele, "Protein Dynamics: From Molecules, to Interactions, to Biology," *Int. J. Mol. Sci.*, vol. 10, No. 3, pp. 1360-1368 (Mar. 2009).

(Continued)

*Primary Examiner* — Gail Verbitsky
(74) *Attorney, Agent, or Firm* — Sunstein Kann Murphy & Timbers LLP

(57) ABSTRACT

An apparatus and methods for characterizing the response of a particle to a parameter that characterizes an environment of the particle. A change is induced in the parameter characterizing the environment of the particle, where the change is rapid on a timescale characterizing kinetic response of the particle. The response of the particle is then imaged at a plurality of instants over the course of a period of time shorter than the timescale characterizing the kinetic response of the particle. The response may be detected by measuring a temperature jump or by measuring correlation and anticorrelation between probe parameters across pixels. More particularly, the particle may be a molecule, such as a biomolecule, and the environment, more particularly, may be a biological cell. The parameter characterizing the environment of the particle may be a temperature, and change may be induced in the temperature by heating a volume that includes the particle, either conductively or radiatively. The volume may be heated by means of a laser, such as an infrared laser, for example, or by microwave heating.

14 Claims, 7 Drawing Sheets

(56) References Cited

U.S. PATENT DOCUMENTS

| | | | | |
|---|---|---|---|---|
| 6,002,136 | A | * | 12/1999 | Naeem ..................... 250/442.11 |
| 6,009,342 | A | * | 12/1999 | Brasch et al. ................. 600/420 |
| 6,546,788 | B2 | * | 4/2003 | Magerle .......................... 73/105 |
| 6,641,708 | B1 | * | 11/2003 | Becker et al. ................. 204/547 |
| 7,050,620 | B2 | * | 5/2006 | Heckman ...................... 382/133 |
| 7,144,553 | B2 | * | 12/2006 | Lewis et al. ................ 422/82.02 |
| 7,452,726 | B2 | * | 11/2008 | Chou et al. ...................... 436/63 |
| 7,476,787 | B2 | * | 1/2009 | Thomas et al. ............... 250/306 |
| 7,510,637 | B2 | * | 3/2009 | Barlow et al. ................. 204/450 |
| 8,134,705 | B2 | * | 3/2012 | Kaduchak et al. ............ 356/337 |
| 8,227,257 | B2 | * | 7/2012 | Ward et al. .................... 436/174 |
| 8,452,576 | B2 | * | 5/2013 | Reich et al. ......................... 703/5 |
| 8,575,566 | B2 | * | 11/2013 | Chen et al. ............... 250/442.11 |
| 2005/0089890 | A1 | * | 4/2005 | Cubicciotti ......................... 435/6 |
| 2007/0053573 | A1 | * | 3/2007 | Rabinovich ................... 382/133 |
| 2008/0286750 | A1 | * | 11/2008 | Xu et al. ............................ 435/4 |
| 2010/0120077 | A1 | * | 5/2010 | Daridon .......................... 435/29 |
| 2012/0071351 | A1 | * | 3/2012 | Fang et al. ....................... 506/10 |
| 2012/0140206 | A1 | * | 6/2012 | Kayani ............................ 356/71 |
| 2013/0000421 | A1 | * | 1/2013 | Ward et al. ...................... 73/863 |
| 2013/0079240 | A1 | * | 3/2013 | Ward et al. ........................ 506/9 |
| 2013/0110040 | A1 | * | 5/2013 | Serpe .......................... 604/93.01 |
| 2013/0222801 | A1 | * | 8/2013 | Harel et al. .................... 356/328 |
| 2013/0292585 | A1 | * | 11/2013 | Gardner .................... 250/504 R |

OTHER PUBLICATIONS

Ignatova et al., "A Method for Direct Measurement of Protein Stability In Vivo," *Protein Structure, Stability, and Interactions, Methods Mol. Biol.*, vol. 490, pp. 165-178 (Jul. 2009).

Jung et al., "Fast Mixing and Reaction Initiation Control of Single-Enzyme Kinetics in Confined Volumes," *Langmuir*, vol. 24, No. 9, pp. 4439-4442 (Mar. 2008).

Kato et al., "Relaxation process after the cooling jump across the pretransition of dipalmitoylphosphatidylcholine bilayers," *Chemistry and Physics of Lipids*, vol. 90, No. 1, pp. 31-44 (Nov. 1997).

Lee et al., "Microscopic magnetic relaxation processes in epitaxial Fe/GaAs(001) mesostructures," *J. Magn. Magn. Mater.*, vol. 226, No. 2002, pp. 1594-1596 (May 2001).

Lee et al., "Statistical Analysis of Fluorescence Correlation Spectroscopy of Ultra Low Concentration Molecules with a Confocal Microscope," *Journal of the Optical Society of Korea*, vol. 12, No. 3, pp. 170-173 (Sep. 2008).

Matsuoka et al., "Statistical Analysis of Lateral Diffusion and Multistate Kinetics in Single-Molecule Imaging," *Biophys. J.*, vol. 97, No. 4, pp. 1115-1124 (Aug. 2009).

* cited by examiner

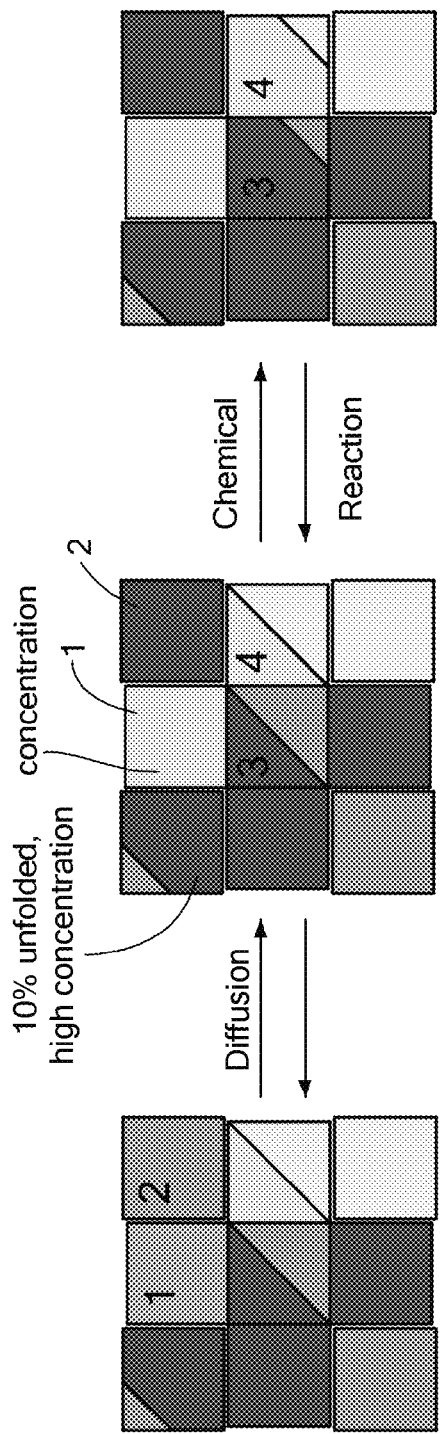
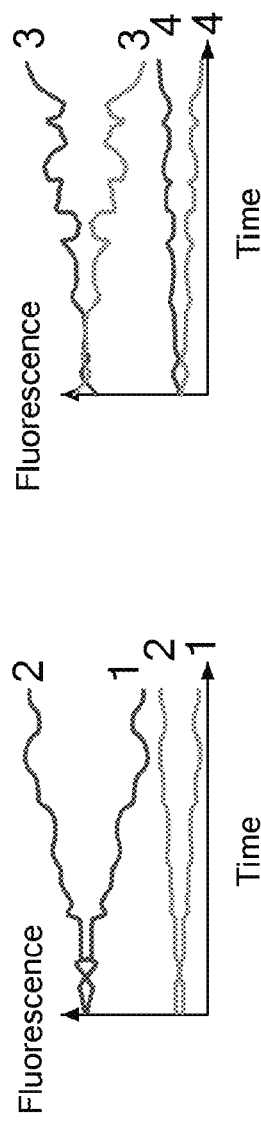
FIG. 6a  FIG. 6b  FIG. 6c  FIG. 6d  FIG. 6e

PARTICLE DYNAMICS MICROSCOPY USING TEMPERATURE JUMP AND PROBE ANTICORRELATION/CORRELATION TECHNIQUES

This invention was made with Government support under Grant MCB 0613643 awarded by the National Science Foundation. The Government has certain rights in the invention.

The present application claims priority from U.S. Provisional Application Ser. No. 61/374,001, filed Aug. 16, 2010, and incorporated herein by reference.

FIELD OF INVENTION

The present invention relates to an apparatus and methods for applying imaging techniques to relaxation dynamics induced in a wide range of systems either by a tailored heating pulse or by imaging of spontaneous fluctuations, and more particularly, to such apparatus and methods as may be applied to biomolecular systems.

BACKGROUND ART

Currently, biomolecular dynamics and stability are investigated predominantly in vitro, on the basis of which findings are extrapolated to explain function in the living cell. The dynamics of biomolecules in vitro are often explained in terms of energy landscapes, usually considered a property of the individual biomolecule, as described by Frauenfelder et al., *The Energy Landscapes and Motions of Proteins*, 254 *Science* 1598-1603 (1991), which is incorporated herein by reference. In the living cell, the biomolecular energy landscape is modulated by myriad interactions. The dynamics and stability of a biomolecule contained within a cell, where it is crowded by up to 400 mg of macromolecules per ml of cytosol, can differ substantially from the dynamics of the isolated biomolecule. Crowding also modifies the properties of cellular water, which, in turn, can couple back to influence the dynamics of biomolecules. Membranes and other large scale structures within the cell can also crowd or confine biomolecules, as can the active interaction with cellular transport machinery or chaperones.

Because of the advantages of studying proteins and other biomolecules within the living cell, several "in-cell" methods have emerged within the last two decades, yielding a variety of types of information. CARS (coherent anti-Stokes Raman scattering) microscopy reports on small molecule distributions inside living cells. FlAsH (fluorescein arsenical hairpin)-labeling can reveal slow urea-induced unfolding of proteins in bacterial cells. FRET (Förster resonant energy transfer) coupled with fluorescence microscopy can localize proteins, monitor protein-protein interactions and the motion of larger protein machinery. Fluorescent tracers coupled to FRAP (fluorescence recovery after photobleaching) or FCS (fluorescence correlation spectroscopy) can monitor diffusion processes on a micrometer length scale. NMR spectroscopy can reveal much detailed information about protein structure and dynamics inside living cells, but unlike the previously enumerated "single-cell" techniques, NMR requires multiple cells to take up isotope enriched proteins to enable detection of the desired protein. In-cell NMR experiments have been successful in yeast, *E. Coli* and mammalian cells.

Additionally, fluorescent tracers used in fluorescence recovery after photobleaching or fluorescence correlation spectroscopy experiments can be used to monitor diffusion processes on a micrometer length scale.

SUMMARY OF EMBODIMENTS OF THE INVENTION

In accordance with embodiments of the present invention, a method is provided for imaging complex structures with an extrinsic probe signal such as, but not limited to, fluorescence, or an intrinsic probe signal, such as, but not limited to, infrared absorption, followed by detection of time-dependent dynamics in the sample. Detection of time-dependent dynamics may be based upon a relaxation induced by a sudden external stress, such as, but not limited to, a temperature jump induced by a shaped heating laser pulse. Detection of time-dependent dynamics may also be based upon imaging natural fluctuations of probe signal and determining the pixel-to-pixel correlations and anti-correlations in the probe signal.

In accordance with further embodiments of the present invention, methods are provided for characterizing the response of a particle to a parameter characterizing an environment of the particle. The methods have steps of:

a. inducing a change in the parameter characterizing the environment of the particle, where the change is rapid on a timescale characterizing kinetic response of the particle; and b. imaging response of the particle to the change at a plurality of instants over the course of a period of time shorter than the timescale characterizing kinetic response of the particle.

In accordance with further embodiments of the invention, the particle may be a molecule, such as a biomolecule, and the environment, more particularly, may be a biological cell. The parameter characterizing the environment of the particle may be a temperature, and change may be induced in the temperature by heating a volume that includes the particle, either conductively or radiatively. The volume may be heated by means of a laser, such as an infrared laser, for example, or by microwave heating.

In yet further embodiments of the present invention, the parameter characterizing the environment of the particle may be a field. The claimed methods may include inducing a temperature gradient by radiative heating of the environment of the particle. The imaging response of the particle may include imaging a fluorescence energy transfer signal with temporal resolution. Imaging the response of the particle may further include correlating a probe response within and between pixels. In that manner, simultaneous measures of particle kinetics and diffusion may additionally be derived.

In accordance with an alternate embodiment of the present invention, an apparatus is provided for characterizing the response of a particle to a parameter characterizing an environment of the particle. The apparatus has a means for changing the parameter characterizing the environment of the particle, rapidly on a timescale characterizing dynamics of the particle, and an imaging system, which may include a camera, for tracking response of the particle to the change at a plurality of instants over the course of a period of time shorter than the timescale characterizing kinetic response of the particle. The apparatus may also have a processor for correlating a pair of probe signals within individual pixels and between pixels.

BRIEF DESCRIPTION OF THE DRAWINGS

Advantages of the present invention and its several improvements will be seen when the following detailed description is read in conjunction with the attached drawings. These drawings are intended to provide a better understanding of the present invention, but they are in no way intended to limit the scope of the invention.

FIG. 2a shows two heating laser profiles, one for an upward jump and one for a downward jump. FIG. 2b shows two corresponding temperature profiles measured directly in a U2OS cell and in vitro by mCherry fluorescence. FIG. 2c plots the ratio (D/A) of donor to acceptor fluorescence, and reflects protein unfolding and refolding in response to induced temperature jumps, in accordance with an embodiment of the invention.

FIG. 3a shows a sigmoid fit to the in vivo D/A ratio upon thermal denaturation, comparing it to in vitro. FIG. 3b shows how the FRET D/A ratio shifts and broadens to an extended population at higher temperature as the protein unfolds.

In FIG. 4a, a T-jump from 27 to 31° C. on the folded baseline shows no unfolding of the less stable PGK after the jump. In FIG. 4b, a T-jump from 39 to 43° C., near the melting temperature, is shown. FIG. 4c shows the response to a T-jump from 49 to 53° C. on the unfolded baseline, showing no further unfolding of the less stable protein.

FIG. 5a shows a folding relaxation trace averaged over a HeLa cell for a T-jump from 39-43° C.; the inset shows a fluorescence image of the HeLa cell. FIG. 5b shows spatially resolved folding relaxation traces in a U2OS cell. FIG. 5c is a color coded image for the three zones in FIG. 5b, while the inset is a fluorescence image of the U2OS cell.

FIGS. 6a-6e demonstrate application of anticorrelation-correlation spectroscopy to simultaneous extraction of diffusion coefficients and reaction rates, in accordance with embodiments of the present invention. Transition from FIGS. 6(a) to 6(b) indicates a transition in correlation of fluorescent emission due to diffusion, while transition from FIGS. 6(c) to 6(b) indicates a transition due to chemical reaction, Correlations of fluorescence within and between adjacent pixels, in the respective cases, are shown in FIGS. 6(d) and 6(e).

DESCRIPTION OF SPECIFIC EMBODIMENTS OF THE INVENTION

Figure 1:
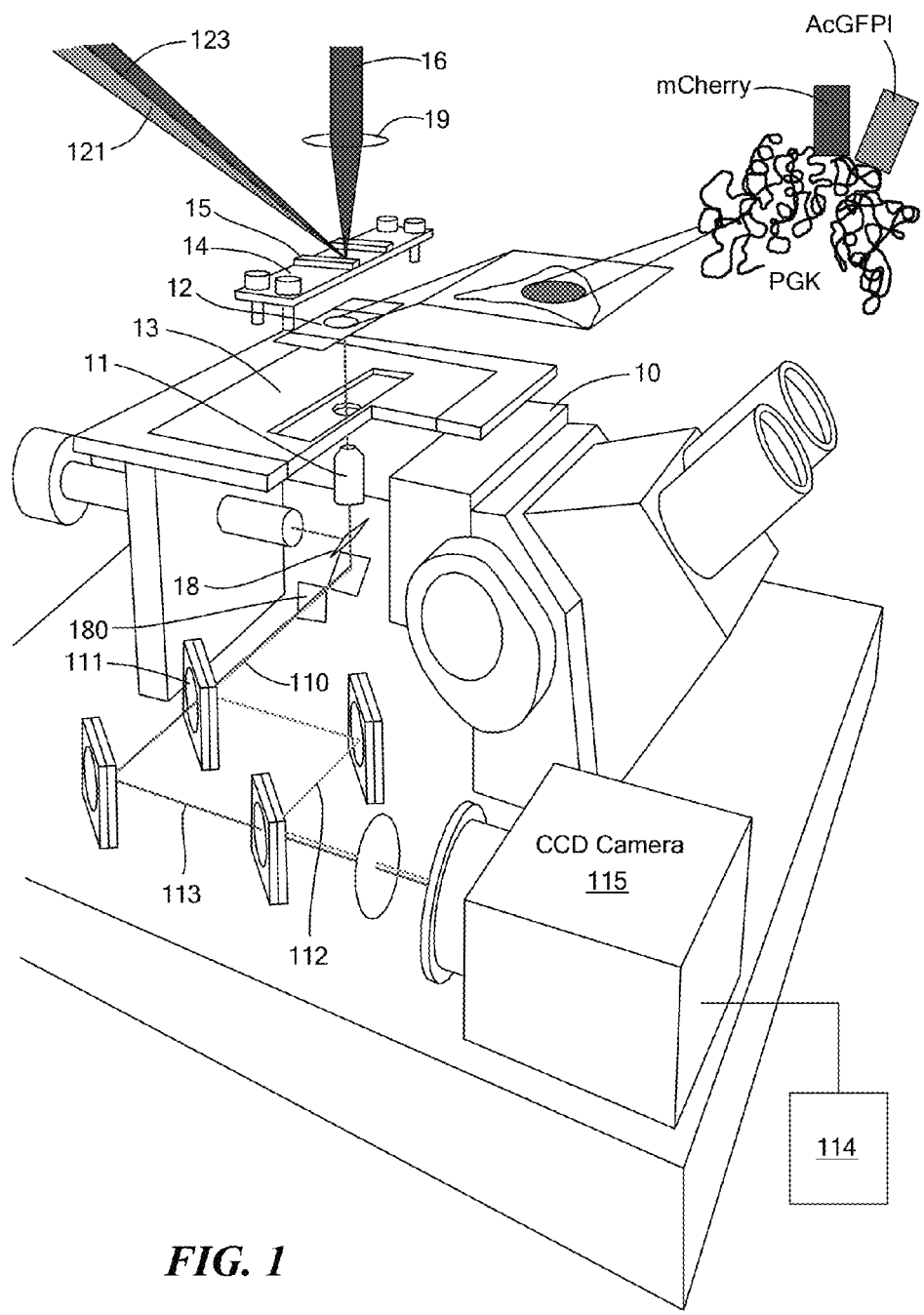
FIG. 1 is a schematic depiction of a temperature jump fluorescence imaging microscope in accordance with embodiments of the present invention.

Definitions. As used in this description and in any accompanying claims, the following terms shall have the meanings indicated, unless the context otherwise requires:

The term "particle," as used herein and in any appended claims, shall mean: an object that is capable of interaction with its environment and that is amenable to analysis according to the methods described herein. As defined herein, proteins and other biomolecules are examples of "particles," as are cells and viruses. More generally, polymeric and inorganic objects generally, including microspheres, microbeads, nanorods and other nanoparticles, quantum dots, etc., all of various shapes and compositions, to include moieties adjoined thereto, are also "particles."

The environment of a particle may be homogeneous, such as a simple fluid, or may be heterogeneous, such as glasses, cells, etc. In heterogeneous environments, methods in accordance with the present invention may advantageously reveal spatial patterns to the kinetic response of particles distributed throughout the environment.

Specific species such as "proteins" and "cells" are used, without limitation, herein as examples of particles. Moreover, it is to be understood that reactions of any sort, between or among particles of any sort, in environments of any sort, homogenous or heterogeneous, are within the scope of the present invention.

As used in this description and in any appended claims, the term "image" shall refer to an ordered representation of scalar or vector quantities corresponding, one-to-one, with spatial positions, referenced either in an absolute frame or relative to a particular body. For example, an image may be an array of values within an electronic memory, or, alternatively, a visual image may be formed on a display device such as a video screen or a printer, or as a pattern of varying optical field intensity and phase in a specified region of space.

"Imaging" is the process of associating quantities, one-to-one, with spatial positions.

Further description of the embodiments of the present invention may be found in Ebbinghaus, et al., *Protein folding stability and dynamics imaged in a living cell*, 7 Nature Methods 319-23 (2010), which is incorporated herein by reference, as are all publications cited on the following pages.

In accordance with preferred embodiments of the present invention, imaging techniques are employed in conjunction with induced temperature jumps to allow high spatio-temporal resolution in probing the response of systems such, for example, as biomolecular dynamics and stability inside a single living cell. The combination of one or more imaging techniques, such as fluorescence microscopy, with temperature jumps, may be referred to herein as Fast Relaxation Imaging (FReI), where it is to be understood that FReI is applicable, as well, to the study of protein-protein interactions, heat-shock responses, and comparative studies of cell populations or whole organisms.

Methods in accordance with the present invention, described herein, may advantageously image fast dynamics of biomolecules in vivo with sub-cellular resolution by coupling imaging techniques, such as time-resolved fluorescence imaging, for example, with either fast temperature jump-induced relaxation kinetics (which may be referred to, herein, as a "relaxation experiment," or by measurements of intensity fluctuations in the image pixels (which may be referred to, herein, as an "anticorrelation-correlation experiment").

An embodiment of the present invention is now described with reference to FIG. 1. Particles studied by methods in accordance with the present invention are imaged, as by an inverted microscope 10 such as a Zeiss Axiovert 100TV. Imaging chambers 12 (typically, glass slides with 100 μm spacers) are mounted on a microscope stage 13 and held in place by a cover plate 14 to provide thermal stability and rapid thermal equilibration. Other imaging chambers may be employed, within the scope of the present invention, such as $CO_2$ environmental chambers, useful for sustaining cells over longer periods, for example. Steady-state heating or cooling may be achieved one or more thermistors 15 or thermoelectric heating or cooling elements, mounted on cover plate 14. A small coupling hole in this plate provides for passage of a heating beam 16, which may be the beam of a laser (not shown) such as an Argon ion laser, or an infrared (IR) heating beam. The coupling hole is preferably sized so as to minimize exposed surface area of the slide and coverslip.

The imaged particles (which may be referred to herein, by way of example, as "cells") are illuminated by an illumination beam 121 derived from a source of light, in any appropriate spectral region, such as a high power LED or by the 458 nm line of an Argon ion laser. The source of illumination beam 121 is preferably mounted on the back of the microscope 10 and collimated using an optical train (not shown) consisting of an aspheric lens and a plano-convex lens. After collimation, illumination beam 121 is passed through an excitation filter (not shown) and focused by a 40× microscope objective, preferably with a numerical aperture of 0.65 or greater.

Emitted two-color fluorescence (from AcGFP1 and mCherry, for example) may be collected by a microscope objective 11 and separated from the blue excitation beam 123 by a dichroic mirror 18 and a longpass emission filter 180. The two-color fluorescence 110 may then be separated into green 112 and red 113 components by using a second dichroic mirror 111 before being simultaneously imaged onto different positions on a CCD camera 115. Typical signal levels, such as those depicted, for example, in FIG. 3, correspond to a column density of <1000 proteins/$\mu m^2$, estimated by comparing cell signal levels with in vitro solutions of protein, with a correction for focal depth of the fluorescence collection.

When using the Argon ion laser for illumination, a prism is used to select the 458 nm line as an illumination beam 121. The illumination beam 121 is passed through a narrow bandpass filter to remove any stray light. In certain embodiments of the invention, the laser illuminates the sample from the top (in a trans-illumination configuration), rather than through the objective. A long focal length lens (f=50 cm, for example) may be used to achieve speckle-free imaging with the laser source, by enlarging the speckles to greater than the size of a cell, or other particle, as discussed below.

Videos of the cell under observation may be recorded. The red and green fluorescence images, projected onto adjacent areas of the same CCD sensor, may be superimposed onto each other with single pixel accuracy. This may be achieved by computing the cross correlation function between the two images, and translating as well as rotating one image to maximize the cross correlation. The mean intensity of each image may be calculated and plotted against the acquisition time for cell-averaged kinetics. Dividing the green by red intensity yields the FRET donor-to-acceptor fluorescence intensity signal (D/A).

Temperature sensing and calibration. The temperature of the sample and its environment may be calibrated both from above (the side of the slide) and below (the side of the coverslip) the stage by thermocouples (not shown). A thermocouple may also provide a feedback signal for the heating resistors 15 to stabilize the temperature to within prescribed limits. Temperature in a living cell may be monitored directly by mCherry fluorescence, or by that of another fluorescent label, to which end a 532 nm diode probe laser may be used in the same configuration as the blue diode, with the probe beam designated by numeral 123 (otherwise referred to herein as the "excitation beam"). The resulting fluorescence is then separated from the excitation light by a bandpass emission filter. As the label's fluorescence intensity is temperature sensitive, it may be calibrated against the stage thermocouples. Additional independent calibration of the temperature of the entire sample height, also suitable for in vitro measurements, may be provided by a 1550 nm laser diode, for example, passed through the sample and typically modulated at 100 kHz for detection by an infrared detector coupled to a lock-in amplifier. Water transmission at 1550 nm is temperature sensitive, and may be similarly calibrated against thermocouples.

Temperature Jump approach. Unfolding and refolding of a fusion protein (as in the Example provided herein), or any other temperature-change-induced effect, may be rapidly initiated (on a timescale short relative to the timescale characterizing dynamics of the particle under study) by any temperature jump induction mechanism. Within the scope of the present invention, any heat transfer mechanism, whether radiative or conductive, may be employed.

Temperature jumps initiated in accordance with the invention, may cover a wide range of time scales. Temperature jumps equilibrate in aqueous media within 2 picoseconds, as shown by Ma et al., *Ultrafast T-jump in water: Studies of conformation and reaction dynamics at the thermal limit*, 128 *J. Am. Chem. Soc.* 6338-40 (2006), and have been carried out with picosecond lasers, nanosecond lasers, as well as slower microwave and resistive heating techniques, as described, for example, by Gruebele, in *Protein folding, misfolding and aggregation*, (Muñoz, ed.) (RSC Publishing, London, 2008), pp. 106-138, which is incorporated herein by reference.

In a preferred embodiment of the invention, described with reference to FIG. 2a, a large-area (denoting the integral of heating power over the course of time) heating pulse is tailored to be applied by a laser, such as an infrared diode laser operating at 2200 nm. A heating beam of the laser output is designated by numeral 16 in FIG. 1. The laser (not shown) may be conveniently mounted above the stage of the inverted microscope. Two representative laser output power profiles 20 and 21 are depicted in FIG. 2a. A laser output power profile may be designed by mapping out the instrument response function with a square pulse (typically on the order of ~ms), followed by Fourier deconvolution of the desired response with the instrument response function. Power profile 20 provides a fast upward temperature jump of 4° C. (with the truncated spike actually extending to 370 mW), while power profile 21 provides a downward jump of less than 50 ms duration. Profile 20 (overshoot+plateau) results in rapid heating followed by a constant temperature for an arbitrary amount of time. Jump resolution of even picosecond duration is within the scope of the present invention, and, at least in some cases, is limited by the response of laser control electronics. Based on the temperature calibration methods described above, it has been demonstrated, for both in vivo and in vitro excitation, that the temperature and temperature jumps may be made uniform, on the requisite temporal scales, to the single pixel level of spatial resolution.

A heating power profile such as depicted by numeral 21 achieves fairly rapid downward jumps with <50 ms time resolution by undershooting the laser power and then ramping it back up to provide an optimal downward step. Cooling of the thin aluminum-covered glass slides can be quite fast. An achromatic lens 19 may be used to focus the heating beam 16 to 500 µm in diameter, allowing uniform heating over 25 times the area of the cell being imaged.

Figure 2A:
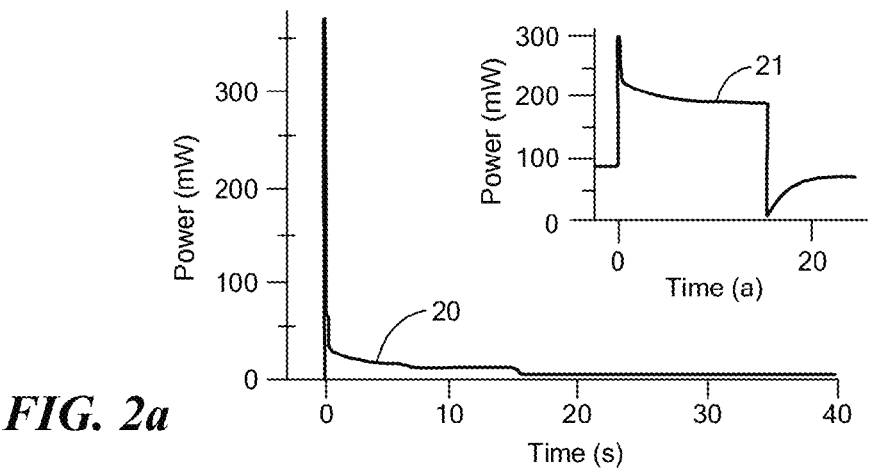
FIGS. 2a-2c present heating laser profiles, resulting temperature profiles, and folding kinetics of the low-melting PGK construct, obtained in accordance with embodiments of the present invention.
Figure 2B:
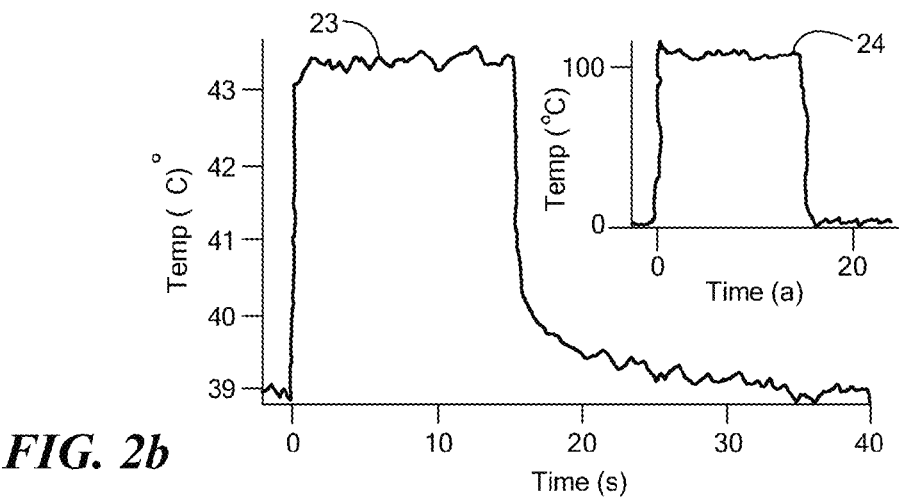
Figure 2C:
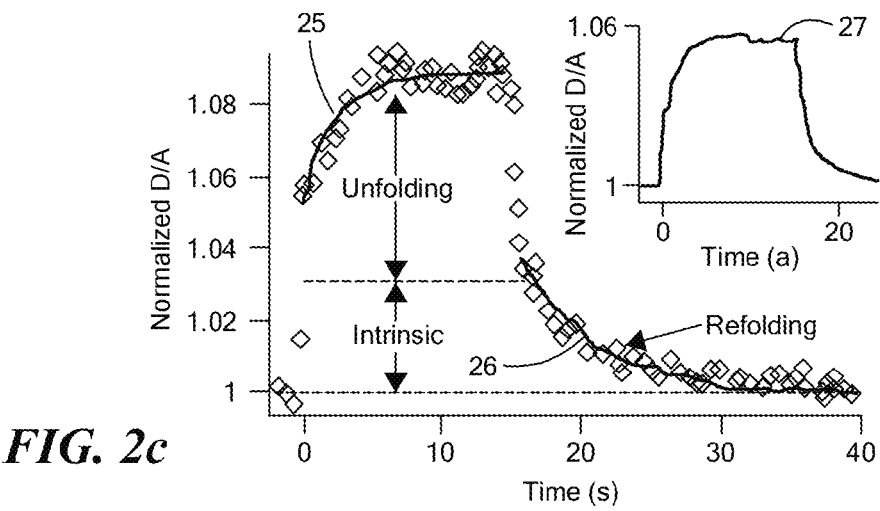

FIG. 2c shows a plot 25 of a normalized D/A ratio reflecting protein unfolding (t=0 s to t=15 s) and subsequently refolding 26 (t=15 s to t=40 s) in a U2OS cell, and also in vitro (plot 27), relative to an intrinsic D/A baseline 28. The initial fast rise contains an unresolved burst phase, and an intrinsic fluorescence baseline. The subsequent resolved phase monitors unfolding of the PGK fusion construct. After the temperature jump is switched off, the protein refolds to the original baseline, indicating complete reversibility both in the cell and in vitro.

It is to be understood that changes in other intensive properties of the environment of the sample particle may be induced in accordance with the present invention, radiatively, or otherwise. Such intensive (or "bulk") properties, other than temperature, may include density (via a pressure jump), partial density (or concentration, via rapid microchannel mixing) of a constituent, viscosity (via dilution), specific gravity, etc., or other intensive thermodynamic properties. A property of the environment changed in accordance with the present invention may be characterized as a field, and may be a scalar, vector, or tensor property of the environment. In all of the above cases, in accordance with various alternate embodiments of the present invention, the dynamic response of a particle is measured microscopically, based on the induced change in intensive property (or "excitation") of the environment of the particle. The resolution of the microscopic measurement is rapid on a timescale characterizing the kinetic response of the particle.

Anticorrelation-Correlation approach. As an alternative fast detection method, anticorrelation and correlation, across mutiple pixels, of the probe signal (e.g. fluorescence, intensities of multiple probes, Raman scattering, or infrared spectrum) may be detected. Fluorescence anticorrelation-correlation spectroscopy (FACS), now described with reference to FIGS. 6(a)-6(e), extends the modality, described heretofore, of relaxation induced by a sudden stress. In the example depicted in FIGS. 6(a)-6(e), a protein is assumed to be labelled so it fluoresces red when folded (R), green when unfolded (G). When protein only diffuses (the transition between FIGS. 6(a) and 6(b)) and protein numbers are small, motion of protein molecules from one pixel to the next will raise the G and R values (a correlated change); when protein folds/unfolds in a pixel, the G and R values change in opposite directions (an anti-correlated change). A kinetic-diffusion model, as described below, can then be used to simultaneously determine the reaction rates (including folding, for example) and diffusion coefficients for every pixel in the image.

In accordance with such embodiments of the present invention, natural fluctuations of the probe signal due to fluctuations in particle number are used as a complimentary technique to relaxation of the probe signal after a fast jump. This scheme differs from conventional fluorescence correlation spectroscopy (FCS), which observes fluctuations in just a single confocal spot in the sample (a single pixel). The single confocal spot approach of the prior art, therefore, misses information that arises because the particle is transported form one pixel to the next when it diffuses, or undergoes spectral changes within the same pixel if it did no diffuse out of the pixel.

An exemplary embodiment of anticorrelation-correlation approach is now described with reference to FIGS. 6(a)-6(e), where fluorescence detection is shown, by way of example. A fast, high-sensitivity camera 115 is used for detection of intensity fluctuations in every pixel of the image, so as to obtain adequate signal-to-noise per pixel per frame, given a Poisson distribution of discrete emissions of fluorescence photons in response to probe beam 123. An example is the Phantom v12.1 camera with a Lambert Research image intensifier, capable of 25% quantum efficiency at 40000 frames per second at 512×512 pixel resolution. Consider a reactive particle that changes color upon reaction, such as the green/red labelled PGK protein discussed above as an example. If such a particle moves, through diffusion, from a first pixel (designated by numeral 1 in FIG. 6(a)) to an adjacent pixel (designated by numeral 2 in FIG. 6(b)), green and red emission (as plotted in FIG. 6(d)) will decrease simultaneously in the first pixel 1, and will increase in the adjacent pixel 2. This is indicated by the lighter hue of pixel 1 in FIG. 6(b), and the darker hue of pixel 2 in FIG. 6(b), relative to FIG. 6(a). The lighter hue indicates a low concentration of a species in a probed state, whereas a darker hue indicates a higher concentration in the probed state. Processor 114 is used to correlate green and red emission within each pixel, and between pairs of pixels, of a frame-by-frame basis. In the case of diffusion of a probed species, the green and red emission in each pixel are correlated, whereas the sum of green and red emission between adjacent pixels is anti-correlated.

Similarly, consider particles that reacts in a patch of several pixels. Green and red emission (as plotted in FIG. 6(e)) will be anticorrelated in each of pixels 3 and 4, but the overall change will be correlated across different pixels, as shown in FIG. 6(b) relative to FIG. 6(c)). Thus, diffusion and reaction produce opposite results, and diffusion and reaction rates can be obtained by using a standard diffusion-reaction model to account for diffusion of molecules among pixels at the same time that molecules undergo reaction. A survey of diffusion-reaction models such as may be employed in the context of the present invention may be found in Matsuoka et al., *Statistical analysis of lateral diffusion and multistate kinetics in single-molecule imaging*, 97 Biophys. J. 1115-24 (2009), which is hereby incorporated by reference. The analysis, in accordance with the present invention and the teachings of the foregoing reference, may advantageously yield a comprehensive picture of kinetics and diffusion in a heterogeneous environment.

Speckle Reduction. Any of various stratagems known for reducing coherence speckles during full imaging with a laser may be employed in practicing the claimed invention, such as those described by Mattheyses et al., *Effective elimination of laser interference fringing in fluorescence microscopy by spinning azimuthal incidence angle*, 69 Microsc. Res. Tech. 642-47 (2006) and by Dingel et al., *Speckle-Free Image in a Laser-Diode Microscope by Using the Optical Feedback Effect*, 18 Opt. Lett. 549-51 (1993), both of which papers are incorporated herein by reference. Alternatively, the illuminating laser may be focused onto the sample in a highly oblique trans-illumination mode with a long focal length (50 cm) lens. This advantageously increases the speckle size relative to the size of the field, uniformly illuminating the sample.

Example

As a demonstration of applying methods in accordance with the present invention, unfolding and refolding of the metabolic enzyme PGK (phosphoglycerate kinase) were investigated. A FRET-labeled fusion construct of PGK was used that unfolded at 39° C. in U2OS (human osteosarcoma) and HeLa (cervical carcinoma) cells. The same construct was also monitored in vitro. The protein was more stable, the thermal denaturation was more gradual, and folding kinetics were slower, in the test cells than in vitro. Because biomolecular interactions are often highly temperature sensitive, methods in accordance with the present invention may advantageously be used to image many fast processes that occur in living cells, such as early events during heat shock response, or protein-protein interactions.

A goal of the demonstration, provided here as an example of practice of the present invention, was to study protein folding within a single cell, using a method whose time resolution is limited only by the induction time of the kinetics, and whose spatial resolution is diffraction-limited. The FReI method, in accordance with embodiments of the present invention, combines fluorescence microscopy of a FRET-labelled protein with small mid-infrared laser-induced temperature jumps.

Imaging two-color fluorescence from a protein labelled with a donor-acceptor pair for FRET detection allows interrogation of the folding status of the construct within a cell by measuring the time evolution of the FRET signal after the temperature jump. Reversible unfolding and refolding may be achieved, as well as temperature titrations across the unfolding transition of the labelled protein while the cell remained alive, as evidenced by cell morphology.

The upper temperature limit of certain embodiments of the invention may be governed by the temperature tolerance of a particular living cell under study. In general, the cell lines used is preferably sufficiently robust as to tolerate small (≤4° C.) temperature jumps, exposure to mid-infrared light (λ≈2000 nm), as well as visible light probing FRET. This should be tolerated by many standard cell lines are sufficiently tolerant, including, for example, the U2OS and HeLa lines used in the example described.

Cells were transfected with plasmids encoding the FRET-labeled protein. Green donor and red acceptor proteins with high melting points (>70° C.) were chosen as labels. Other colors or labeling techniques, such as dye labeling followed by microinjection, are within the scope of the present invention. Cells containing the FRET-labeled protein are adhered to a slide on a temperature-controlled stage during the course of the method, in accordance with the description above referring to FIG. 1.

Two strategies that can be used to excite the FRET donor include excitation in the blue or the ultraviolet. For example, a high power blue LED may be employed, or a 458 nm Argon ion laser line. In a preferred embodiment, the LED epi-illuminates the sample through an aspheric lens, beam-combining filters, and the main microscope objective. The Argon ion laser is preferably used for experiments that require high-excitation intensities (low protein expression). Using an Argon ion laser in epi-illumination leads to a speckled image, so this approach has historically been used only for confocal or single molecule-particle tracking experiments, and not for full cell imaging.

As described above, red and green fluorescence were collected through the objective and beam combining filters, then split into a red and a green channel and imaged onto adjacent spots of a single CCD sensor. A camera frame was recorded every 16.7 ms, in fact, the frame rate, rather than the temperature jump rate, limited the time resolution of the experiment, and could easily be sped up by using cameras with microsecond time resolution.

To study kinetics, fast upward and downward laser temperature jumps were initiated in the cell and its surrounding aqueous medium by a computer-tailored infrared diode laser, as described above.

The temperature profile was monitored pixel-by-pixel in vitro or directly within the cell by exciting the acceptor label with a green diode laser, the green diode laser beam designated by numeral 123 in FIG. 1. The acceptor fluorescence intensity ("A") was calibrated to an absolute temperature scale with a thermocouple mounted on the stage or on the slide below the cell. In the example described, the temperature was uniform to single pixel resolution, however, implementation of temperature gradients across the cell, in order to induce differential stress, for example, is within the scope of the present invention.

For small jumps, the protein unfolding and refolding kinetics are completely reversible and return to the same D/A baseline within the cell, as shown in FIG. 2c. The initial very fast rise of D/A is due to a combination of an intrinsic fluorescence baseline 33 (shown in FIG. 3a), and a small sub-ms kinetic burst phase, resolved in previous in vitro studies. The subsequent time-resolved increase of D/A results from unfolding of the protein construct. At least for the U2OS and HeLa cells studied in the examples described herein, irreversible effects caused by aggregation or heat shock response are observed only for much larger temperature jumps and much longer heating times than the 15 second, 4° C. temperature steps used in the demonstration. Slow infrared heating up to 60° C. has been used to study heat shock response and gene induction in vivo.

Figure 3A:
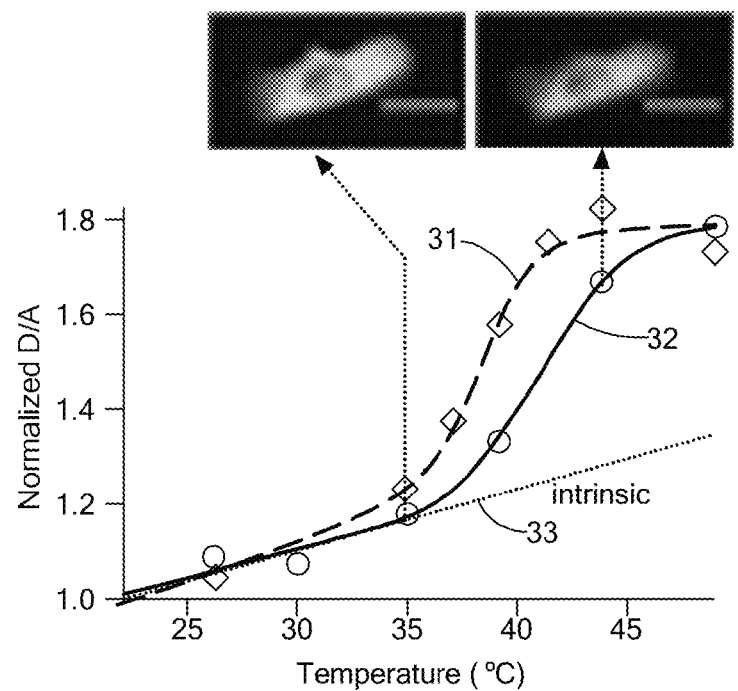
FIGS. 3a-3b show temperature-dependent FRET and thermal denaturation of a low-melting PGK fusion construct.
Figure 3B:
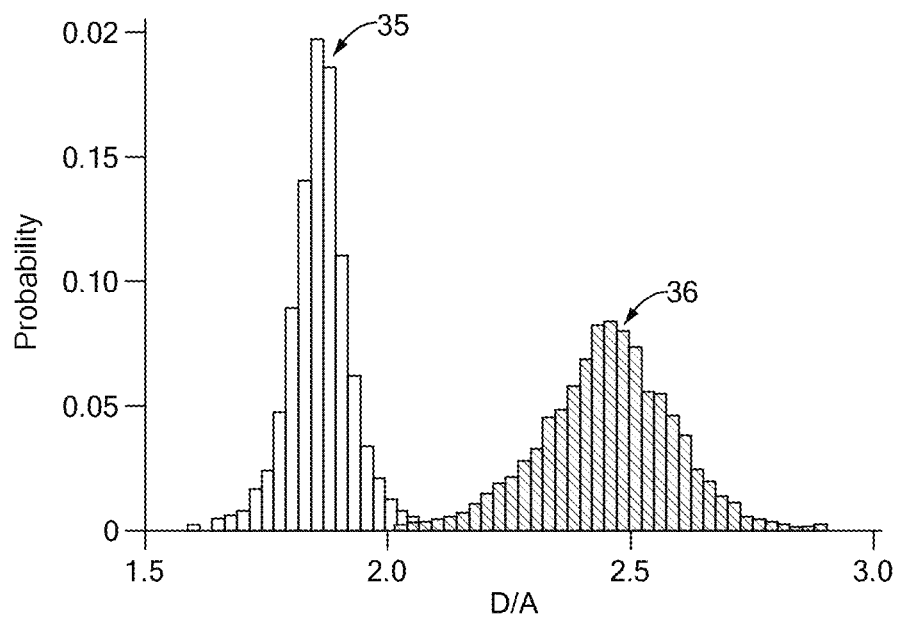

Because different cells have different ratios of intact fusion, construct to construct, with mCherry improperly folded or bleached, all data were referenced to the D/A ratio at 23° C., leading to the normalized D/A scales depicted in FIGS. 2, 3 and 4. For comparison of in vitro to in vivo profiles, the former amplitude was also normalized to the latter. For FIGS. 3a and 5a, red and green fluorescence images were overlaid to obtain the pseudo-colored images. Pseudo color was obtained by adding the original 8 bit values in the red (R) and green (G) fluorescence channels into an RGB color (R,G, 0).

In a typical FReI experiment, the cell is gradually heated on the stage and a heat denaturation curve of the protein is recorded as D/A ratio within a few minutes. At each steady-state temperature, a small jump (typically 4° C.) then measures the relaxation kinetics. To account for inactive acceptor labels, the data is referenced to a low temperature (23° C.) where most protein is folded. Thus stability and kinetic data can be collected in the same experiment on one cell. Importantly, denaturation transitions and lifetime measurements are insensitive to absolute fluorescence variations across the cell caused by different cell thicknesses, for example.

The unfolding and refolding of PGK in readily cultured U2OS (human osteosarcoma) cells is described with reference to FIGS. 2-5. The invention was employed to understand how kinetics of unfolding in cells differed from in vitro conditions. PGK was chosen for the presently described demonstration because previous in vitro experiments revealed stretched exponential kinetic phases ranging from microseconds to minutes. Thus, substantial unfolding within the experimental time window (16 ms to 15 s) was to be expected.

A fusion protein was created, consisting of mutant PGK labelled on its N- and C-termini by AcGFP1 (green donor) and mCherry (red acceptor), respectively. A low-melting triple mutant (Y122W/W308F/W333F) of PGK was employed. This construct advantageously allows for the study of unfolding titrations and kinetics at near-physiological temperatures that are not harmful to the U2OS cells and that avoid the heat shock response.

A high-melting double mutant (W308F/W333F, $T_m$>45° C.) was used as a reference that would not unfold below 45° C. The fluorescent labels did not unfold up to 70° C. in vitro (cell death is the in vivo upper temperature limit). Cell morphology served as an indicator of viability in all experiments, allowing temperatures up to 49° C. to be reached in these cells.

To measure protein stability in the cell and monitor folding, the D/A ratio of the PGK fusion protein construct was measured as a function of temperature, relative to the D/A ratio at 23° C. The FRET ratio shows the expected broadening and shift caused by unfolding through several intermediates at higher temperature; as the protein unfolds the N- and C-termini move further away from each other, leading to a decrease in FRET in the D/A ratio distribution at 44° C. (designated generally by numeral 36 in FIG. 3b) relative to the D/A ratio distribution at 33° C. (designated generally by numeral 35). The D/A ratio traces out a sigmoidal unfolding curve with increasing temperature, both in vitro (curve 31 in FIG. 3a) and in vivo (curve 32). Methods in accordance with the invention indicate that unfolding is more gradual, and stability is slightly greater, in the cell; the melting temperature, $T_m$, of the protein in cells was 42° C. vs. 39° C. in solution). It was thus expected that temperature jumps starting at 39° C. should lead to observable kinetics, while temperature jumps in the baselines (below 30° C. or above 45° C.) would yield only a small instantaneous response of the completely folded or completely unfolded protein. The signal to noise shown in FIGS. 3 and 4 required a protein column density of about $1000/\mu m^2$ in the cell.

Figure 4A:
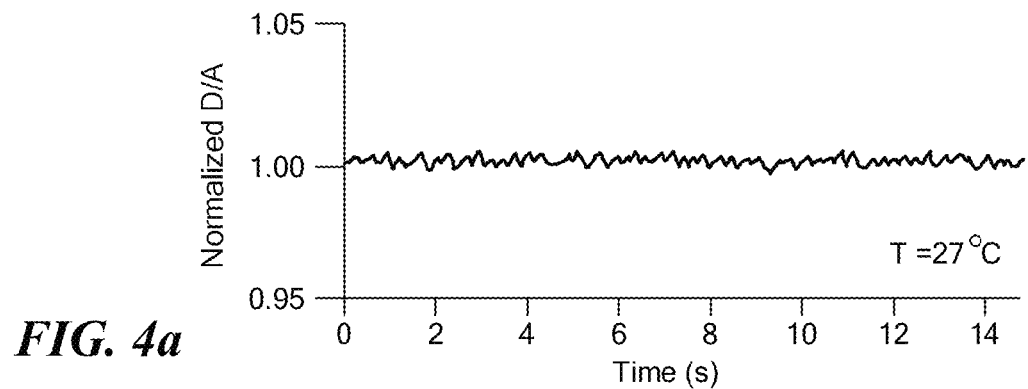
FIGS. 4a-4c show normalized D/A relaxation kinetics of the PGK fusion protein in vivo and in vitro.
Figure 4B:
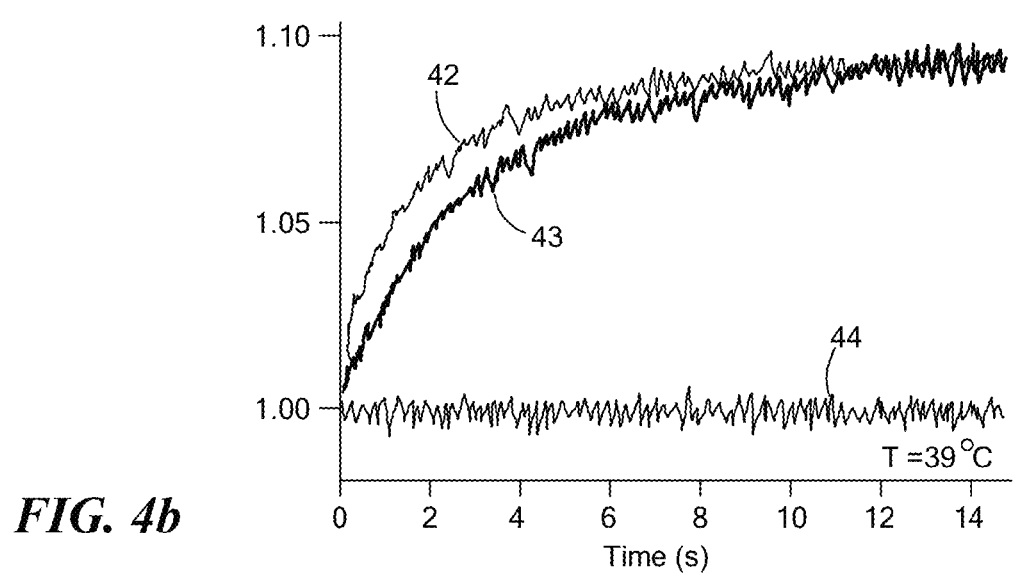
Figure 4C:
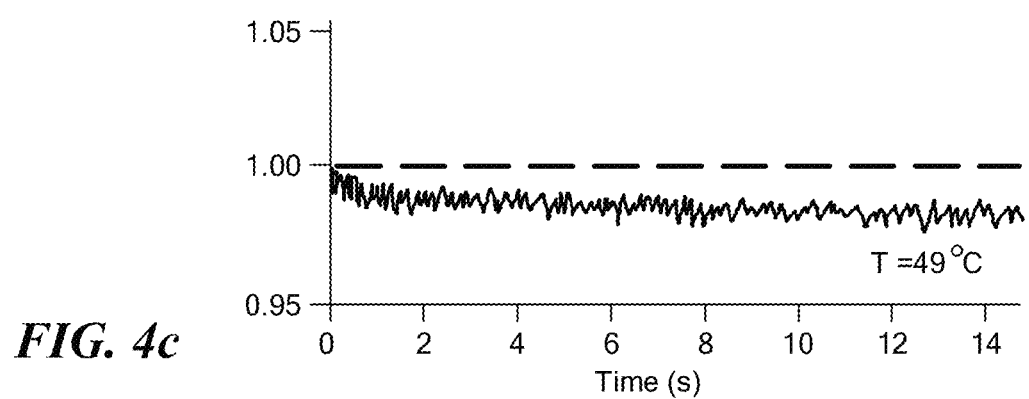

Unfolding 25 and refolding 26 kinetics of the low-melting PGK mutant are shown in FIG. 2c, starting at different initial temperatures, but with the same T-jump magnitude of 4° C. Very different responses are observed at 27° C., 39° C. and at 49° C., as shown in FIGS. 4a, 4b, and 4c, respectively. As expected from the thermodynamic measurements, jumping from an initial temperature of 27° C. yielded no response, as shown in FIG. 4a, because no protein unfolding took place. Jumping from 39° C. by 4° C., a large change in the D/A ratio is resolved as the protein thermally unfolds. The D/A ratio resolves unfolding of the less stable construct in vitro (plot 42) and in vivo (plot 43), but not for the more stable mutant (plot 44). The unfolding signal may be well described by a signal function $S(t)=A \exp[-(t/\tau)^\beta]$, yielding a time constant of $\tau=3.01\pm0.04$ s. (Uncertainties quoted herein correspond to 2 s.d.) The stretching factor $\beta$ allowed a simplified fit to multi-intermediate kinetics and yielded values in the range 0.67-0.87 in all cases.

As shown in FIG. 4c, jumping the temperature from 49° C. yielded only a small, fast, decrease in D/A after the jump. This was due to a small amount of aggregation at high temperature, which causes intermolecular FRET and therefore a decrease of D/A. The high-melting PGK mutant had no kinetic phase at 39° C., as apparent in trace 44 shown in FIG. 4b.

The same temperature jump experiments were repeated with the low-melting PGK construct in aqueous solution at pH 7, and observed faster kinetics. Subsequent to a jump from 39° C., a relaxation time of $\tau=1.95\pm0.22$ s was observed. Thus, the environment in the cytoplasm of this particular cell slows down the unfolding kinetics.

Figure 5A:
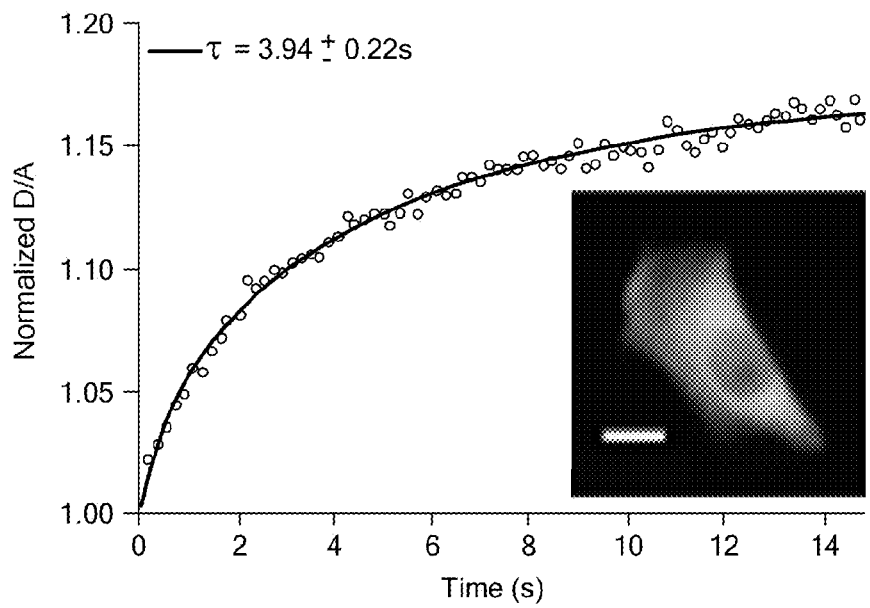
FIGS. 5a-5c compare folding kinetics of the less stable PGK mutant in two cell lines.
Figure 5B:
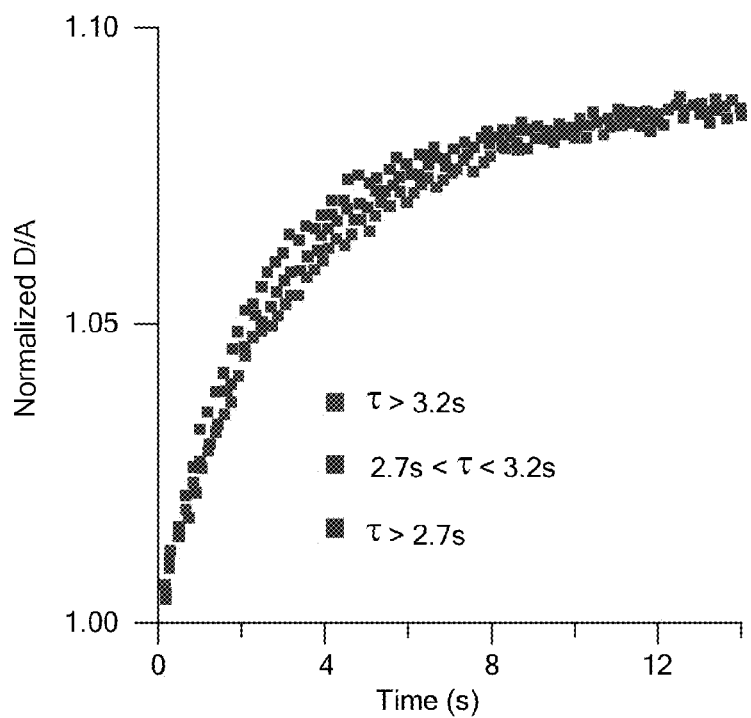
Figure 5C:
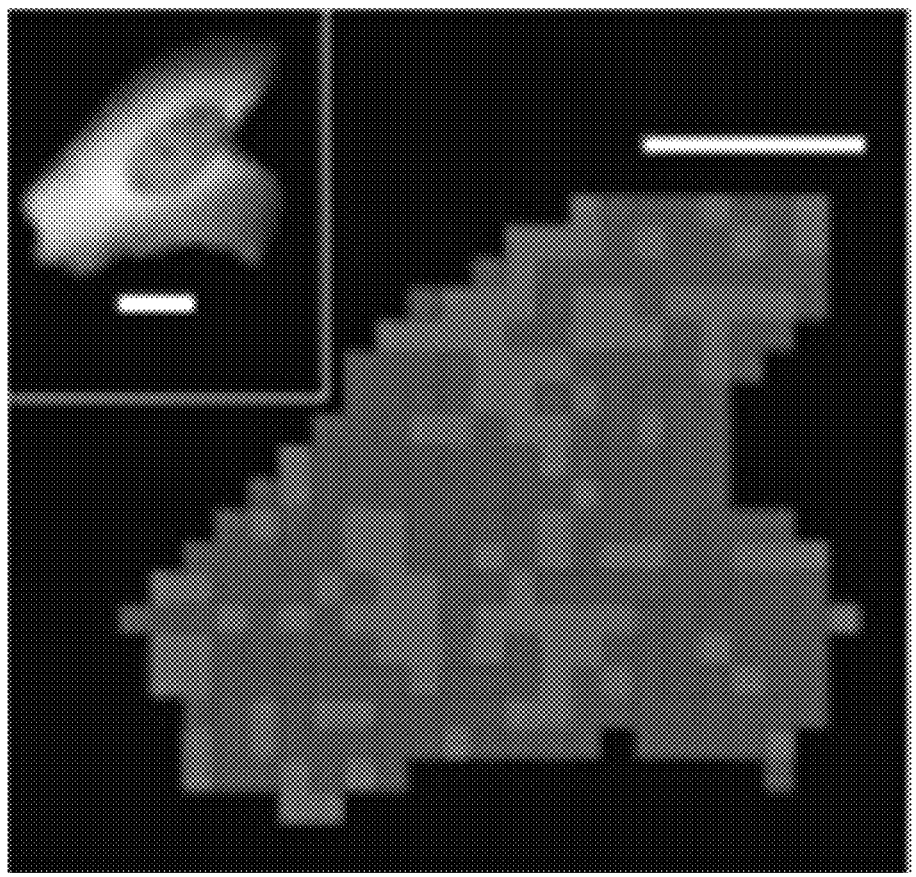

As now described with reference to FIGS. 5a and 5b, the in vivo experiment in U2OS was the repeated in HeLa cells to show that different cell lines can be used in accordance with the present invention. As shown in FIG. 5a, the kinetics in the HeLa cell were slowed down even more ($\tau=3.94\pm0.22$ s) compared to the in vitro value. FIG. 5b distinguishes zones of fast (<2.7 s, blue), medium (2.7-3.2 s, indigo) and slow (>3.2 s, red) folding. Finally, an image of the U2OS cell, depicted in FIG. 5c, shows distinctions among cytoplasmic regions of short (<2.7 s), medium (2.7 to 3.2 s) and long (>3.2 s) unfolding times within the same cell. The largest homogenous regions are ≈8 μm in diameter.

Methods practiced in accordance with embodiments of the present invention, thus, permit comparison of the behavior of the same protein construct inside a single living cell directly with dilute solution. In accordance with alternate embodiments of the invention, different expression levels coupled with diffraction-limited resolution of the thermodynamics may be used to probe the extent to which the cytoplasm modulates protein stability.

It is to be understood that any time-dependent process that can be induced by a change of a thermodynamic parameter can be observed by FReI, indeed, FReI may be applied to inorganic particles. For certain processes physiological temperature limits may pose less of an experimental hindrance. Tracking cell-specific protein dynamics in entire cell populations may be employed advantageously to study processes like stochastic gene expression, cell division or apoptosis. Rapid temperature sensitive protein-protein interactions or aggregate formation within cells may be perturbed and monitored as they relax back towards steady-state. Similarly, systems of particles may be monitored as they approach a new equilibrium configuration. For example, inorganic heterogeneous systems such as colloids or glasses, may be imaged as they undergo phase transitions after sudden switching of a thermodynamic variable.

In accordance with further embodiments of the present invention, in vivo kinetic assays may be developed in organisms amenable to microscopy studies. For example, temperature-sensitive small molecule binding may be used for drug screening or searching for compounds that act as protein misfolding medication, and fundamental processes such as the heat shock response may be studied in vivo.

The embodiments of the invention described herein are intended to be merely exemplary; variations and modifications will be apparent to those skilled in the art. All such variations and modifications are intended to be within the scope of the present invention as defined in any appended claims.

We claim:

1. A method for characterizing response of a particle to a parameter characterizing an environment of the particle, the environment localized in both space and time, the method comprising:
   a. retaining the localized environment of the particle within an imaging chamber;
   b. inducing a change in the parameter characterizing the environment of the particle, where the change is rapid on a timescale characterizing kinetic response of the particle; and
   c. imaging response of the particle to the change at a plurality of instants over the course of a period of time shorter than the timescale characterizing kinetic response of the particle.

2. A method according to claim 1, wherein the particle is a molecule.

3. A method according to claim 1, wherein the environment is a biological cell.

4. A method according to claim 1, wherein the parameter characterizing the environment of the particle is a temperature.

5. A method according to claim 4, wherein the step of inducing a change in the parameter characterizing the environment of the particle includes conductively heating the environment that includes the particle.

6. A method according to claim 4, wherein the step of inducing a change in the parameter characterizing the environment of the particle includes radiatively heating the environment that includes the particle.

7. A method according to claim 6, wherein radiatively heating the environment comprises heating with a laser.

8. A method according to claim 6, wherein radiatively heating the environment comprises heating with an infrared laser.

9. A method according to claim 6, wherein radiatively heating the environment comprises microwave heating.

10. A method according to claim 1, wherein the parameter characterizing the environment of the particle is a field.

11. A method according to claim 1, wherein imaging response of the particle includes imaging a fluorescence energy transfer signal with temporal resolution.

12. A method according to claim 1, wherein imaging response of the particle includes correlating a probe signal within and between pixels.

13. A method according to claim 12, further comprising deriving simultaneous measures of particle kinetics and diffusion.

14. A method according to claim 1, further comprising inducing a temperature gradient by radiative heating of the environment of the particle.

\* \* \* \* \*